US011723564B1

(12) United States Patent
Shverdin et al.

(10) Patent No.: US 11,723,564 B1
(45) Date of Patent: Aug. 15, 2023

(54) OPTICAL SENSOR LIGHT FILTERING IN A WEARABLE DEVICE

(71) Applicant: AMAZON TECHNOLOGIES, INC., Seattle, WA (US)

(72) Inventors: Miro Yakov Shverdin, Mountain View, CA (US); Nevzat Akin Kestelli, San Jose, CA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 277 days.

(21) Appl. No.: 17/164,353

(22) Filed: Feb. 1, 2021

(51) Int. Cl.
*A61B 5/1455* (2006.01)
*A61B 5/0205* (2006.01)
*A61B 5/00* (2006.01)
*G01J 3/51* (2006.01)
*A61B 5/024* (2006.01)
*A61B 5/332* (2021.01)

(52) U.S. Cl.
CPC ........ *A61B 5/14552* (2013.01); *A61B 5/0205* (2013.01); *A61B 5/7278* (2013.01); *G01J 3/51* (2013.01); *A61B 5/02433* (2013.01); *A61B 5/332* (2021.01); *A61B 5/681* (2013.01); *A61B 2562/0238* (2013.01); *A61B 2562/043* (2013.01); *A61B 2562/185* (2013.01)

(58) Field of Classification Search
CPC . A61B 5/14552; A61B 5/0205; A61B 5/7278; A61B 5/02433; A61B 5/332; A61B 5/681; A61B 2562/0238; A61B 2562/043; A61B 2562/185; A61B 5/145; G01J 3/51
See application file for complete search history.

(56) References Cited

U.S. PATENT DOCUMENTS

| 10,517,517 | B2 * | 12/2019 | Schipper et al. | .. A61B 5/02416 |
| 11,051,706 | B1 * | 7/2021 | Nadeau | ................ A61B 5/1455 |
| 2015/0011851 | A1 * | 1/2015 | Mehta | .................. A61B 5/6898 600/324 |
| 2019/0000331 | A1 | 1/2019 | Han | |
| 2019/0000399 | A1 * | 1/2019 | Quinn | ................ A61B 5/02125 |

OTHER PUBLICATIONS

"Band-stop filter", Wikipedia, 4 pages. Retrieved from the Internet: URL: https://en.wikipedia.org/wiki/Band-stop_filter.

(Continued)

*Primary Examiner* — Eric F Winakur
*Assistant Examiner* — Abid A Mustansir
(74) *Attorney, Agent, or Firm* — Lindauer Law, PLLC

(57) ABSTRACT

A compact optical sensor is used to determine heart rate, hemoglobin, hydration, peptides, or oxygen saturation using a light source and a single photodiode. The single photodiode has a first filter and a second filter. The first filter is closer to the light source and is transparent to green light and blocks red light. The second filter is farther from the light source and is transparent to red light and blocks green light. This arrangement of the filters facilitates acquisition of backscattered light from desired depths of measurement within the body of a user. At a first time, the light source emits red light and first output from the photodiode is determined. At a second time, the light source emits green light and second output from the photodiode is determined. The optical sensor determines oxygen saturation using the first output and heart rate using the second output.

20 Claims, 9 Drawing Sheets

(56) References Cited

OTHER PUBLICATIONS

"Flat-Top Comb Filters Data Sheet", Optoplex Corporation, 2 pgs. Retrieved from the Internet: URL: http://optoplex.com/download/Optoplex%20Flat-Top%20Comb%20Filter%20Brochure_2020EN.pdf.
"Flat-Top Comb Filters", Optoplex Corporation, 2 pgs. Retrieved from the Internet: URL: http://optoplex.com/Comb_Filter.htm.
"VEMD8080 Data Sheet", Vishay, Apr. 24, 2018, Revision1.0. 7 pgs. Retrieved from the Internet: URL: https://www.vishay.com/docs/84565/vemd8080.pdf.

* cited by examiner

OPTICAL SENSOR LIGHT FILTERING IN A WEARABLE DEVICE

BACKGROUND

Physiological data may be used to help a user manage their health, make more informed decisions, and improve the quality of their life. For example, physiological data such as heart rate, blood oxygen levels, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
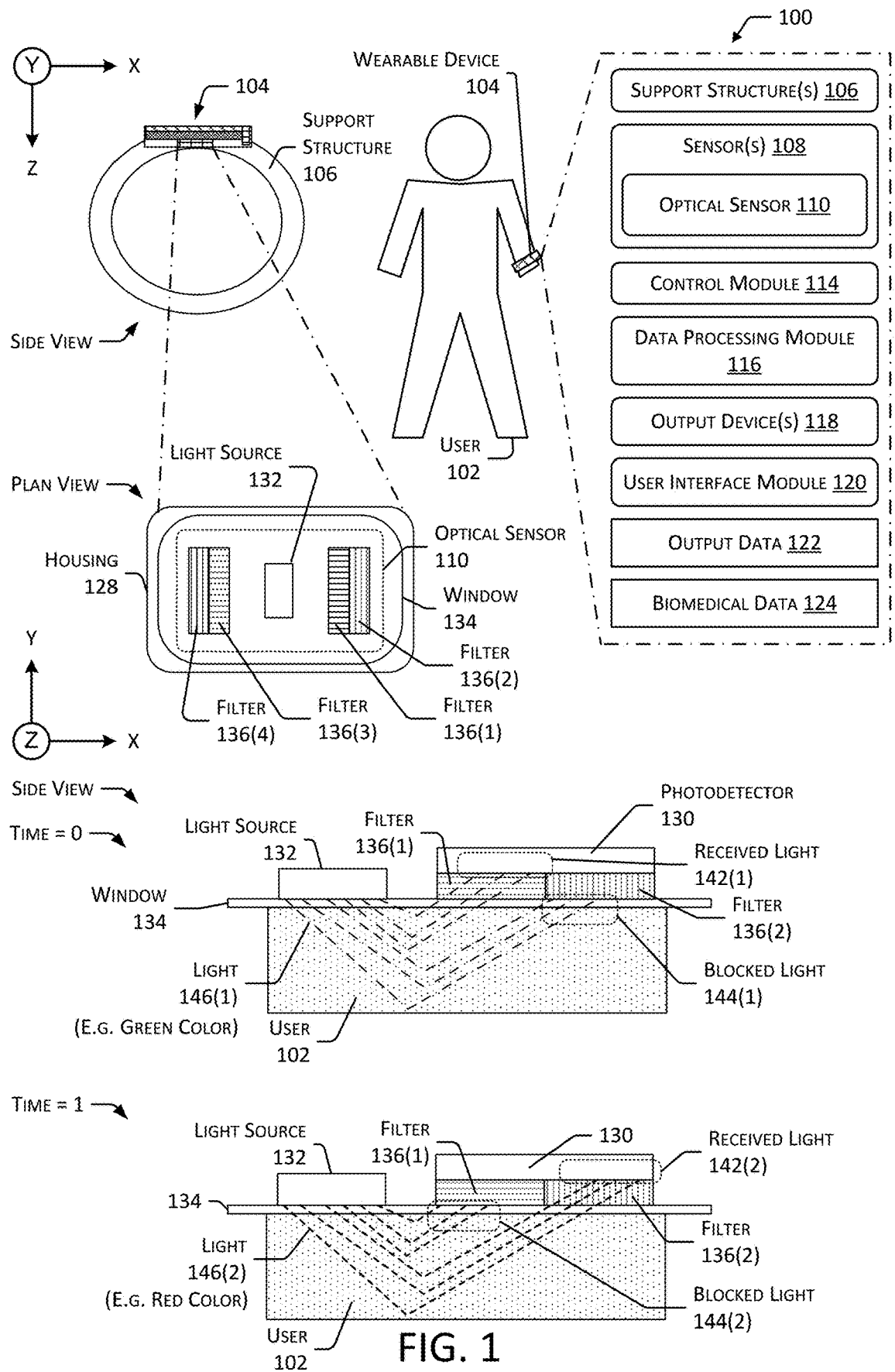
FIG. 1 is an illustrative system that includes a user and a wearable device that uses an optical sensor to determine biomedical data, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

The structures depicted in the following figures are not necessarily according to scale. Furthermore, the proportionality of one component to another may change with different implementations. In some illustrations the scale or a proportionate size of one structure may be exaggerated with respect to another to facilitate illustration, and not necessarily as a limitation.

DETAILED DESCRIPTION

A wearable device may be an important part of a healthy lifestyle. Wearable devices include sensors that may be used to determine different types of biomedical data to provide a user with different kinds of health information. For example, the wearable device may use an optical sensor to determine a user's heart rate, which may be indicative of heart function or cardiovascular fitness at different levels of physical activity. As another example, the wearable device may use the optical sensor to determine a measure of oxygen saturation levels in a user's blood, which may be indicative of how well the user's body can absorb and use the oxygen breathed in. The oxygen breathed in by a user is transported to red blood cells through the lungs. The wearable device may also use the optical sensor to measure hemoglobin levels, which may be indicative of an iron deficiency or anemia. The wearable device may also use the optical sensor to measure fat levels, which may be used to provide information or guidance with respect to a user's fitness goals.

Described in this disclosure are determinations of different kinds of biomedical data by using a single optical sensor comprising multiple filters. An optical sensor may comprise a light source and at least one photodetector. In the context of a wearable device, limitations on device size may restrict a type or quantity of sensors included in the wearable device. Wearable devices are generally compact enough to provide for user comfort. By having a single optical sensor usable to determine different types of biomedical data, a user may have more health information available as compared to a wearable device that relies on multiple optical sensors to provide the same health information. An additional benefit from using a single optical sensor to determine different kinds of biomedical data is a reduction in production costs because the single optical sensor may be used instead of multiple optical sensors.

Different wavelengths of light travel through a user's body and reflect or otherwise scatter in different ways. Such reflectance and scattering of light after light penetrates a user's body may be referred to as diffuse reflectance. In traditional wearable devices, different sensors may be used to detect different wavelengths of light. Determining biomedical data from reflected light may depend on a distance between a light source and an optical sensor. For example, in such a traditional wearable device, there may be a first optical sensor and a second optical sensor. In this traditional wearable device, the first optical sensor may have a first distance between a light source and a photodetector, where the first distance is greater than a second distance between a light source and a photodetector in the second optical sensor. In this traditional wearable device, the first optical sensor may be used to detect green light usable to determine a heart rate, and the second optical sensor may be used to detect red/IR light usable to determine blood oxygen levels. Distances between a light source and an optical sensor depend on optimizing a received signal for a particular wavelength of light.

In this disclosure, distances between a light source and a photodetector in an optical sensor may be defined by a combination of a distance between the light source and on locations of one or more filters applied to a light-sensitive area of the photodetector. For example, a photodetector may be coated with one or more filters. The one or more filters may be a multilayer dielectric coating applied to a light-sensitive area of an optical sensor. Individual filters of the one or more filters may be transmissive to an individual range of light wavelengths. In some examples, a housing may comprise an optical sensor, where the housing comprises a window that makes contact with the skin of a user. In this example, the window may be coated with the one or more filters, where the different filters may be transmissive to an individual range of wavelengths of light.

Continuing with this example, a first filter may be a short-pass filter that is transmissive to green wavelengths, and a second filter may be a long-pass filter that is transmissive to red wavelengths and infrared (IR) wavelengths. A short-pass filter may be applied to a photodetector as a short-pass dielectric coating. A long-pass filter may be applied to a photodetector as a long-pass dielectric coating. In other examples, the first filter or the second filter may be a bandpass filter or a non-dielectric filter. To improve the receipt of reflected green wavelengths of light, the first filter is applied to a first area of the light-sensitive area that is closer to the light source. Similarly, to improve the receipt of reflected red or IR wavelengths of light, the second filter is applied to a second area of the light-sensitive area that is farther from the light source. In this example, without any filters, the optical sensors may be sensitive to wavelengths of both green light and red light. With respect to the diffuse reflectance of light emitted by the wearable device 104 light source, different wavelengths of light have different penetration depths at which the wavelength of light is reflected sufficiently for a signal quality associated with an accurate determination of biometric data.

By using a single optical sensor to determine optical signals from multiple light wavelengths, the number of optical sensors used by a wearable device may be reduced. A reduction in the number of optical sensors may reduce a quantity of independent channels that an analog front end may need to control. The reduction in the number of optical sensors may also allow for tighter or more controlled spacing between IR/red and green channels.

The wearable device may include a control module that coordinates generation of light and determinations of biomedical data based on determinations of an intensity of light received at a photodetector of an optical sensor. In some examples, because a photodetector may be sensitive to multiple wavelengths of light associated with multiple colors, determinations of biomedical data based on light received at the photodetector may use time multiplexing.

For example, at a first time, the control module may both: (1) operate a light source of an optical sensor to generate a first color of light, and (2) determine an intensity of light received at a photodetector of the optical sensor. The control module interprets all light received at the photodetector as the color of light generated by the light source. Similarly, at a second time, the control module may both: (1) operate the light source of the optical sensor to generate a second color of light, and (2) determine an intensity of light received at the photodetector of the optical sensor. The control module interprets all light received at the second time at the photodetector as the color of light generated by a light source.

In some implementations, a portion of a wearable device that comes in contact with a user may comprise a first housing that is a field replaceable unit. The first housing may comprise a first optical sensor, where the first optical sensor includes a first light source and a first photo detector located at a first location relative to the first light source. Different users may have different body compositions and different body characteristics. In general, the distance between a photodetector and a light source may result in a different quality of a received optical signal at a light-sensitive area through one or more filters.

To provide for customizations that improve determinations of biomedical data, the first housing may be replaced by a second housing, where the second housing comprises a second optical sensor that has different distances between a second light source and the filter areas of a second photodetector. In this example, the distance in the second optical sensor between the second light source and the filter areas of the second photodetector may result in improved signal quality received at the light-sensitive areas through the one or more filters.

The wearable device in this disclosure may be an important part of a healthy lifestyle based on providing biomedical data to a user within a device that is a comfortable size. For example, biomedical data such as heart rate, blood oxygen levels, and so forth may be useful for health management. Because the wearable device provides determinations of different kinds of biomedical data by using multiple filters used by a single optical sensor, the wearable device may be used to help a user manage their health, make more informed decisions, and improve the quality of their life.

ILLUSTRATIVE SYSTEM

FIG. 1 is an illustrative system 100 that includes a user 102 and a wearable device 104 with electronic circuitry that uses an optical sensor 110 to determine biomedical data, according to one-implementation.

The user 102 may be wearing a wearable device, wearable device 104. The wearable device 104 may be implemented in various physical form factors including, but not limited to, the following: wrist bands, torcs, arm bands, ankle bands, abdominal straps, and so forth.

A control module 114 may be used to direct operation of hardware or software components of the wearable device 104. For example, the control module 114 may comprise a hardware processor executing instructions that operate the optical sensor 110. The optical sensor 110 may use a light source 132 and a photodetector 130 to determine a heart rate, blood oxygenation levels, a respiratory rate, or other physiological values or biomedical data 124 of the user 102. In this example, the optical sensor 110 comprises two photodetectors and two filters for each photodetector, where filters 136(1, 2) are associated with a first photodetector 130, and where filters 136(3, 4) are associated with a second photodetector. For clarity, a side view of the second photodetector is not depicted in FIG. 1. In other examples, the optical sensor 110 may comprise one photodetector or more than two photodetectors, where each photodetector is associated with respective one or more filters.

The optical sensor 110 may use optical components, including a light source 132 and a photodetector 130, to detect blood volume changes in the microvascular bed of tissue. For example, the control module 114 may operate the optical sensor 110 to use the light source 132 to illuminate the skin of the user 102 and may measure changes in light absorption. Changes in light absorption may be caused by the perfusion of blood throughout the skin. In some cases, the control module 114 may operate the optical sensor 110 to measure a pressure pulse due to the distension of arteries caused by each cardiac cycle. The change in volume caused by the pressure pulse may be detected by illuminating the skin with light, such as light from a light source 132 that includes one or more light emitting diodes (LEDs), and measuring the amount of light that reaches the photodetector 130. An example photodetector 130 may be a photodiode. The photodetector 130 may be a semiconductor device that converts light into an electrical current.

A plan view of a portion of the wearable device 104 depicts a housing 128. The housing 128 comprises an optical sensor 110 and a window 134. The filters 136(1, 2) may be applied to a surface of a light-sensitive area of the photodetector 130. For example, the photodetector 130 may be coated with one or more filters 136(1, 2). The one or more filters 136(1, 2) may be a multilayer dielectric coating applied to the light-sensitive area of the photodetector 130. Individual filters of the one or more filters 130 may be transmissive to an individual range of light wavelengths. In some examples, the housing 128 may comprise the optical sensor 110, where the housing 128 comprises a window 134 that makes contact with the skin of a user 102. In this example, the window 134 may be coated with the one or more filters 130, where the one or more filters 130 may be transmissive to an individual range of wavelengths of light.

The photodetector 130 may have a light-sensitive area associated with different portions of the light-sensitive area. A first filter 136(1) may be applied to a first portion of the light-sensitive area and a second filter 136(2) may be applied to a second portion of the light-sensitive area. In some examples, the first filter 136(1) and the second filter 136(2) may be adjacent and non-overlapping. In other examples, a transition between filters may be a gradient. A gradient transition may be more cost-effective to manufacture in comparison to adjacent, non-overlapping filters.

The first filter 136(1) may be a short-pass filter that is transmissive to green wavelengths, and the second filter 136(2) may be a long-pass filter that is transmissive to red wavelengths and infrared (IR) wavelengths. A green wavelength emitted by the light source 132 and detected by the photodetector 130 may be 520-545 nanometers (nm) or 495-570 nm. A red wavelength emitted by the light source 132 and detected by the photodetector 130 may be 640-700 nm or 400-700 nm. An IR wavelength emitted by the light source 132 and detected by the photodetector 130 may be 850 nm-1 micron. A yellow wavelength emitted by the light source 132 and detected by the photodetector 130 may be 570-590 nm. To improve the receipt of reflected green wavelengths of light, the first filter is applied to a first area of the light-sensitive area that is closer to the light source. Similarly, to improve the receipt of reflected red or IR wavelengths of light, the second filter is applied to a second area of the light-sensitive area that is farther from the light source. In this example, the optical sensor 110 comprises two photodetectors, but in other implementations of a wearable device 104, there may be a single photodetector or more than two photodetectors. A wearable device 104 may also comprise one or more optical sensors 110, where different optical sensors may comprise different types of filters coating one or more photodetectors.

In this example, at a first time, time=0, the control module 114 may operate the light source 132 to generate a first color of light 146(1). The first color of light 146(1) may be associated with wavelengths of light indicative of a green color. The light 146(1) emitted from the light source 132 may penetrate the skin of the user 102 and some portion of the emitted light 146(1) is reflected toward the photodetector 130. The reflected light 146(1) may pass through the window 134 and be received at the two filters 136(1, 2). Filter 136(1) allows the first color of light 146(1) to be received at the first portion of the light-sensitive area of the photodetector 130, and the allowed light is depicted as received light 142(1). Filter 136(2) blocks the first color of light 146(1) from being received at the second portion of the light-sensitive area of the photodetector 130, and the blocked light is depicted as blocked light 144(1). During normal operation, the window 134 may be in contact with or near the skin of the user 102.

In some examples, filter 136(1) may filter out most, but not all, wavelengths of light that are not the first color of light 146(1). Similarly, in some examples, filter 136(2) may filter out most, but not all, wavelengths of light that are not the second color of light 146(2). For example, say filter 136(1) is transmissive to 99% of the first color of light 146(1) and transmissive of 3% of the second color of light 146(2). In this example, filter 136(1) and filter 136(2) are applied to a different 50% of the light-sensitive area of the photodetector 130. Similarly, in this example, filter 136(2) is transmissive of 99% of the second color of light 146(2) and transmissive of 3% of the first color of light 146(1). In other examples, other percentages may be representative of an effectiveness of a particular filter at blocking out light outside of a wavelength associated with the particular filter. The control module 114, given an amount of an emitted color of light transmissive by a particular filter and an amount of light that the other filters are transmissive of an emitted color of light, may determine an amount of light that should be blocked that has not been blocked. Based on the amount of light that should be blocked that has not been blocked, the control module 114 may adjust an optical signal for each emitted color of light.

The control module 114 may determine, based on the received light 142(1) at the photodetector 130, first data indicative of an intensity of the first color of light 146(1) received at the first time. In this example, the light source 132, at the first time, does not operate LEDs of a different color. Because at the first time only the green light 146(1) is generated, all detected light at the photodetector 130 is determined to be green light 146(1). The first data may be used to determine a heart rate of the user 102.

At a second time, time=1, the control module 114 may operate the light source 132 to generate a second color of light 146(2). The second color of light 146(2) may be associated with wavelengths of light indicative of a red color. The light 146(2) emitted from the light source 132 may penetrate the skin of the user 102 and some portion of the emitted light 146(2) is reflected toward the photodetector 130. The reflected light 146(2) may pass through the window 134 and be received at the two filters 136(1, 2). Filter 136(2) allows the second color of light 146(2) to be received at the second portion of the light-sensitive area of the photodetector 130, and the allowed light is depicted as received light 142(2). Filter 136(1) blocks the second color of light 146(2) from being received at the first portion of the light-sensitive area of the photodetector 130, and the blocked light is depicted as blocked light 144(2).

The control module 114 may determine, based on the received light 142(2) at the photodetector 130, second data indicative of an intensity of the second color of light 146(2) received at the second time. In this example, the light source 132, at the second time, does not operate LEDs of a different color. Because at the second time only the red light 146(2) is generated, all detected light at the photodetector 130 is determined to be red light 146(2). The second data may be used to determine a blood oxygen level of the user 102.

The optical sensor 110 may also be used to monitor breathing, hypovolemia, and various circulatory conditions of the user 102. In some cases, the optical sensor 110 may be used to measure blood pressure and may operate in conjunction with a temperature sensor for measuring a temperature of the user 102. Biomedical data 124 may include blood pressure, heart rate, or blood oxygen levels that may be used as input to a data processing module 116 to provide health information to the user 102.

The wearable device 104 may include at least one support structure 106 that supports one or more components. For example, the wearable device 104 may comprise a housing or capsule that is attached to a wrist band, allowing the wearable device 104 to be retained on the wrist of the user 102, as shown in FIG. 1. The wrist band is depicted as a support structure 106. In another example, the wearable device 104, or a portion thereof, may comprise an adhesive patch to adhere to the user 102 during operation of the wearable device 104. Also shown in FIG. 1 is a side view of the wearable device 104 as shown worn on the arm of user 102.

The wearable device 104 may include, or receive data from, one or more other sensors 108. For example, a temperature sensor may be used to provide an indication of the body temperature of the user 102. The body temperature may then be used as an input to the data processing module 116 to provide health information to the user 102. These sensors 108 are discussed in more detail below with regard to FIG. 2. Data from the sensors 108 may be obtained to provide other information about physiological status, activity level, and so forth.

Output from the sensors 108 may also be used to determine operation of the data processing module 116. For example, the sensors 108 may include one or more accelerometers. If the accelerometers detect motion that exceeds a threshold value, the data processing module 116 may be operated to determine biomedical data 124. For example, if the user 102 has been running, the system 100 may operate to determine heart rate or blood oxygen levels. In another example, if the motion of the user 102 is less than a threshold value, the data processing module 116 may operate to determine other biomedical data. For example, if no movement has been detected for 2 minutes, such as if the user 102 is asleep or unconscious, the data processing module 116 may be operated to determine blood glucose levels.

A user interface module 120 may be configured to use biomedical data 124 and produce output data 122. For example, based on biomedical data 124 indicating that the blood glucose level is below a threshold value, output data 122 may be generated. Similarly, the data processing module 116 may determine, based on the biomedical data 124, that a heart rate is below a third threshold or above a fourth threshold, or that blood oxygen levels are outside of a specified range of values. One or more output devices 118 may be used to present a user interface based on at least a portion of the output data 122. Continuing the example, the user interface module 120 may produce output data 122 that comprises instructions to operate a speaker to present an audible prompt indicating the biomedical data 124.

In another example, the output data 122 may be provided to another device (not depicted). For example, the wearable device 104 may be connected via Bluetooth or another wireless protocol to a smartphone, a wireless access point in a vehicle computer system, or some other device. Based on the output data 122, the other device may present an output to the user 102, alert some other user, modify operation of the other device, and so forth. For example, if the wearable device 104 provides data to a vehicle that indicates the user 102 in the driver's seat has a concentration of alcohol that exceeds a threshold value, or that some other component of the biomedical data 124 is outside a given range, the vehicle may be prevented from moving, or may only be able to operate in a fully autonomous mode.

In some implementations, the wearable device 104 may comprise an additional reference photodetector that is not exposed to light. The reference photodetector may be similar or identical in construction to the photodetector 130. Because the reference photodetector is not exposed to the exterior, it may be mounted within the wearable device 104 in any conveniently dark location, does not require access to an exterior window, and thus minimizes construction cost. For example, the reference photodetector may have a light-sensitive area that is not exposed to an outer surface of the wearable device 104. Any electrical current detected from the photodetector that is not exposed to light may be used to calibrate the photodetector 130 to compensate for any electrical current generated due to exposure of the photodetector 130 to ambient light. The output from the reference photodetector may be used to compensate for noise produced by the photodetector 130.

The control module 114 may determine first data indicative of a first difference between the first output from the photodetector 130 and third output from the reference photodetector. Similarly, second data indicative of a second difference between the second output from the photodetector 130 and the third output may be determined. The control module 114 may use the third output to adjust the first output and the second output to take into account noise produced by the reference photodetector that is deemed to be similar to noise produced by the photodetector 130, improving the accuracy of the output. The resulting data may then be used to determine the biomedical data 124. For example, the first data and the second data, that include adjustments for noise as indicated by the reference photodetector, may then be used to determine biomedical data 124.

In some implementations, ambient light levels may be determined by determining output from the photodetector 130 while the light source 132 is inactive and not providing light. For example, at a third time, time=2, the control module 114 may turn off the light source 132 and determine third output from the photodetector 130 at the third time. The control module 114 may determine first data indicative of a first difference between the first output and third output, as well as a second data indicative of a second difference between the second output and the third output. The control module 114 may use the third output to adjust the first output and the second output to take into account ambient light, improving the accuracy of the output. The resulting data may then be used to determine the biomedical data 124. For example, the first data and the second data, that include adjustments for ambient light, may then be used to determine biomedical data 124.

In some implementations, ambient light levels may be determined based on output from a photodetector that has no filters. For example, the photodetector 130 may be a first photodetector and housing 128 may comprise a second photodetector (not depicted). The second photodetector may be a same type or may be a same part number as the first photodetector. In this example, at the first time, time=0, the control module 114 may determine output from the second photodetector in addition to determining output from the first photodetector. In this example, at the first time, the light source 132 emits the first color of light 146(1) comprising wavelengths of light indicative of a green color. Output from the second photodetector may be third output. The third output may include ambient light in addition to detected light from diffuse refraction of the emitted first color of light 146(1). In this example, first biomedical data may be determined based on the first output and the third output. The first biomedical data may be a heart rate. Similarly, at the second time, the second photodetector may determine fourth output, and second biomedical data may be determined based on the second output and the fourth output. The second biomedical data may be a blood oxygenation level.

In some implementations, the optical sensor 110 may be used to determine biomedical data 124 using fluorescence.

For example, at a first time the light source 132 may emit light 146 at a first wavelength that may stimulate a first chemical species in the user 102 to fluoresce at a second wavelength. Continuing the example, at a second time the light source 132 may emit light 146 at a third wavelength that may stimulate a second chemical species in the user 102 to fluoresce at a fourth wavelength. The filter 136(1) may pass the second wavelength while the filter 136(2) may pass the fourth wavelength. Using this technique, the optical sensor 110 is able to acquire data about different fluorescent wavelengths.

The optical sensor 110 may be used in other combined modes as well. For example, reflectance of a first wavelength of light may be measured at a first time while fluorescence of a second wavelength may be measured at a second time.

Figure 2:
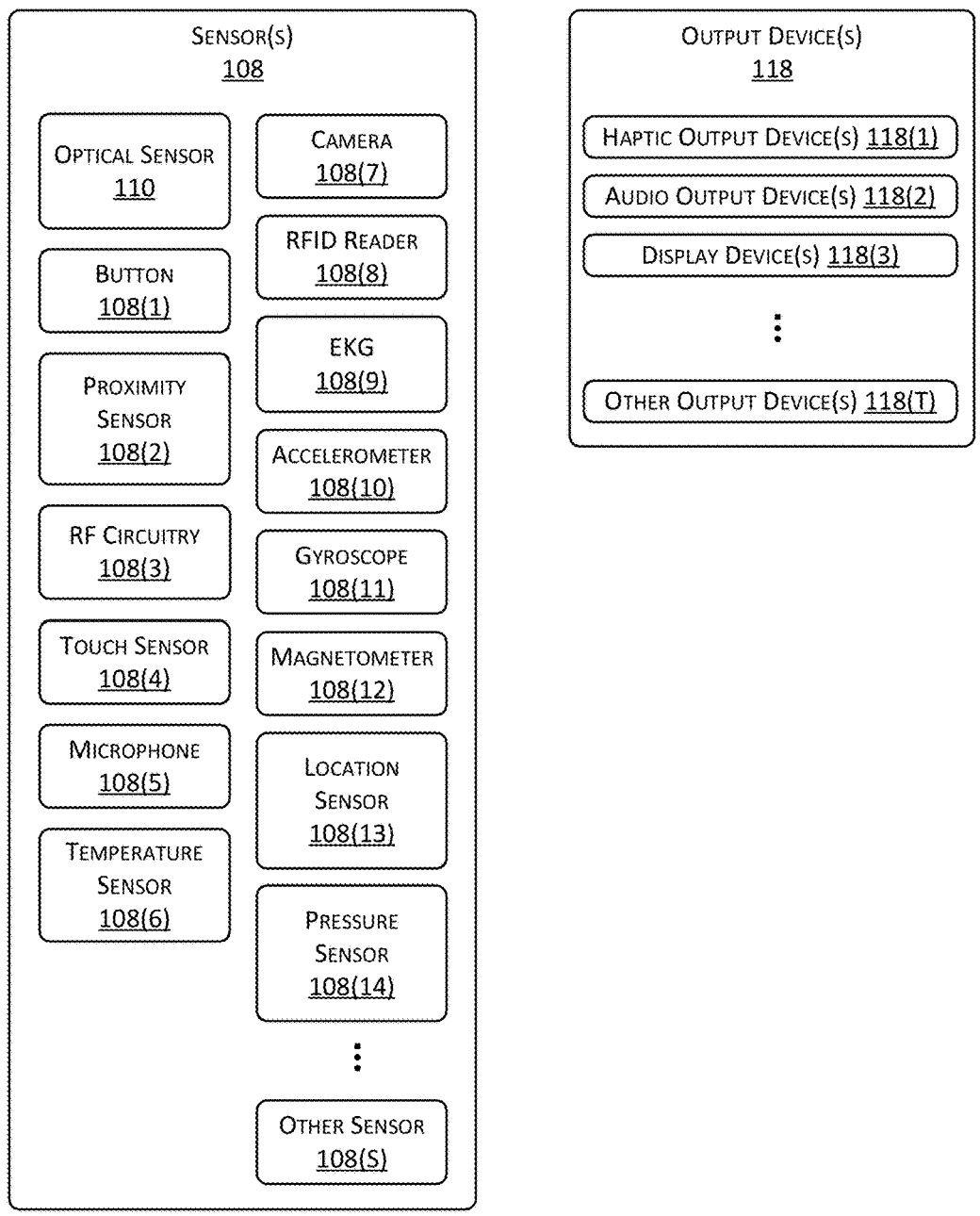
FIG. 2 illustrates a block diagram of sensors and output devices that may be used by a wearable device during operation, according to one implementation.

FIG. 2 illustrates a block diagram 200 of sensors 108 and output devices 118 that may be used by the wearable device 104 of the system 100 during operation.

The wearable device 104 may include one or more sensors 108 integrated with or internal to the wearable device 104. For example, the sensors 108 may be built-in to the wearable device 104 during manufacture. The wearable device 104 may also include output devices 118 to communicate with devices external to, but in communication with, the wearable device 104 using Bluetooth, Wi-Fi, 4G, 5G, LTE, ZigBee, Z-Wave, or another wireless or wired communication technology.

The one or more sensors 108 may include one or more buttons 108(1) that are configured to accept input from the user 102. The buttons 108(1) may comprise mechanical, capacitive, optical, or other mechanisms. For example, the buttons 108(1) may comprise mechanical switches configured to accept an applied force from a touch of the user 102 to generate an input signal.

A proximity sensor 108(2) may be configured to provide sensor data 324 indicative of one or more of a presence or absence of an object, a distance to the object, or characteristics of the object. The proximity sensor 108(2) may use optical, electrical, ultrasonic, electromagnetic, or other techniques to determine a presence of an object. For example, the proximity sensor 108(2) may comprise a capacitive proximity sensor configured to provide an electrical field and determine a change in electrical capacitance due to presence or absence of an object within the electrical field.

The sensors 108 may include radio frequency (RF) circuitry 108(3).

The sensors 108 may include one or more touch sensors 108(4). The touch sensors 108(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

The sensors 108 may include one or more microphones 108(5) that may be configured to acquire information about sound present in the environment. In some implementations, arrays of microphones 108(5) may be used. These arrays may implement beamforming techniques to provide for directionality of gain. The one or more microphones 108(5) may be used to acquire audio data, such as speech from the user 102.

A temperature sensor (or thermometer) 108(6) may provide information indicative of a temperature of an object.

The temperature sensor 108(6) may be configured to measure ambient air temperature proximate to the user 102, the body temperature of the user 102, and so forth. The temperature sensor 108(6) may comprise a silicon bandgap temperature sensor, thermistor, thermocouple, or other device. In some implementations, the temperature sensor 108(6) may comprise an infrared detector configured to determine temperature using thermal radiation.

The sensors 108 may include one or more cameras 108(7). The cameras 108(7) may comprise a charge couple device, complementary oxide semiconductor, or other image sensor that is able to acquire images.

The sensors 108 may include one or more radio frequency identification (RFID) readers 108(8), near field communication (NFC) systems, and so forth. The user 102, objects around the wearable device 104, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise an RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 108 may include an electrocardiograph (EKG) 108(9) that is configured to detect electrical signals produced by the heart of the user 102.

The sensors 108 may include one or more accelerometers 108(10). The accelerometers 108(10) may provide information such as the direction and magnitude of an imposed acceleration. Data such as rate of acceleration, determination of changes in direction, speed, and so forth, may be determined using the accelerometers 108(10).

The sensors 108 may include a gyroscope 108(11). The gyroscope 108(11) provides information indicative of rotation of an object affixed thereto. For example, the gyroscope 108(11) may indicate whether the device has been rotated.

The sensors 108 may include a magnetometer 108(12). The magnetometer 108(12) may be used to determine an orientation by measuring ambient magnetic fields, such as the terrestrial magnetic field. For example, output from the magnetometer 108(12) may be used to determine whether the wearable device 104 comprising the sensor 108 has changed orientation or otherwise moved. In other implementations, the magnetometer 108(12) may be configured to detect magnetic fields generated by another device.

The sensors 108 may include a location sensor 108(13). The location sensor 108(13) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 108(13) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 108(13) may be omitted or operate in conjunction with an external resource such as a cellular network operator providing location information, or Bluetooth beacons.

The sensors 108 may include a pressure sensor 108(14). The pressure sensor 108(14) may provide information about the pressure between a portion of the wearable device 104 and a portion of the user 102. For example, the pressure sensor 108(14) may comprise a capacitive element, strain gauge, spring-biased contact switch, or other device that is used to determine the amount of pressure between the user's 102 arm and an inner surface of the wearable device 104 that is in contact with the arm. In some implementations the pressure sensor 108(14) may provide information indicative of a force measurement, such as 0.5 Newtons, a relative force measurement, or whether the pressure is greater than a threshold value.

In some implementations, operation of one or more components in the wearable device 104 may be based at least in part on information from the pressure sensor 108(14). For example, based on data provided by the pressure sensor 108(14) a determination may be made as to whether at least a portion of the wearable device 104 is in contact with the user 102 or another object. Continuing the example, if the pressure indicated by the pressure sensor 108(14) exceeds a threshold value, the wearable device 104 may be determined to be in contact with the user 102. Based on this determination that the wearable device 104 is in contact with the user 102, one or more of a transmitter, receiver, sensors 108, optical sensor 110, and so forth may be operated. Likewise, data from the pressure sensor 108(14) may be used to determine that the wearable device 104 is not in sufficient physical contact with the user 102. As a result, one or more of the transmitter, a receiver, sensors 108, or optical sensor 110, and so forth may be turned off.

The sensors 108 may include other sensors 108(S) as well. For example, the other sensors 108(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 108 may include hardware processors, memory, and other elements configured to perform various functions. Furthermore, the sensors 108 may be configured to communicate by way of a network or may couple directly with the wearable device.

The wearable device may include one or more output devices 118. The output devices 118 are configured to generate signals which may be perceived by the user 102, detectable by the sensors 108, or a combination thereof.

Haptic output devices 118(1) are configured to provide a signal, which results in a tactile sensation to the user 102. The haptic output devices 118(1) may use one or more mechanisms such as electrical stimulation or mechanical displacement to provide the signal. For example, the haptic output devices 118(1) may be configured to generate a modulated electrical signal, which produces an apparent tactile sensation in one or more fingers of the user 102. In another example, the haptic output devices 118(1) may comprise piezoelectric or rotary motor devices configured to provide a vibration that may be felt by the user 102.

One or more audio output devices 118(2) are configured to provide acoustic output. The acoustic output includes one or more of infrasonic sound, audible sound, or ultrasonic sound. The audio output devices 118(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 118(2).

The display devices 118(3) may be configured to provide output that may be seen by the user 102 or detected by a light-sensitive detector such as an image sensor or light sensor. The output may be monochrome or color. The display devices 118(3) may be emissive, reflective, or both. An emissive display device 118(3), such as using light emitting diodes (LEDs), is configured to emit light during operation. In comparison, a reflective display device 118(3), such as using an electrophoretic element, relies on ambient light to present an image. Backlights or front lights may be used to illuminate non-emissive display devices 118(3) to provide visibility of the output in conditions where the ambient light levels are low.

The display mechanisms of display devices 118(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 118(3) may operate as panels, projectors, and so forth.

The display devices 118(3) may be configured to present images. For example, the display devices 118(3) may comprise a pixel-addressable display. The image may comprise at least a two-dimensional array of pixels or a vector representation of a two-dimensional image.

In some implementations, the display devices 118(3) may be configured to provide non-image data, such as text or numeric characters, colors, and so forth. For example, a segmented electrophoretic display device, segmented LED, and so forth, may be used to present information such as letters or numbers. The display devices 118(3) may also be configurable to vary the color of the segment, such as using multicolor LED segments.

Other output devices 118(T) may also be present. For example, the other output devices 118(T) may include scent or odor dispensers.

Figure 3:
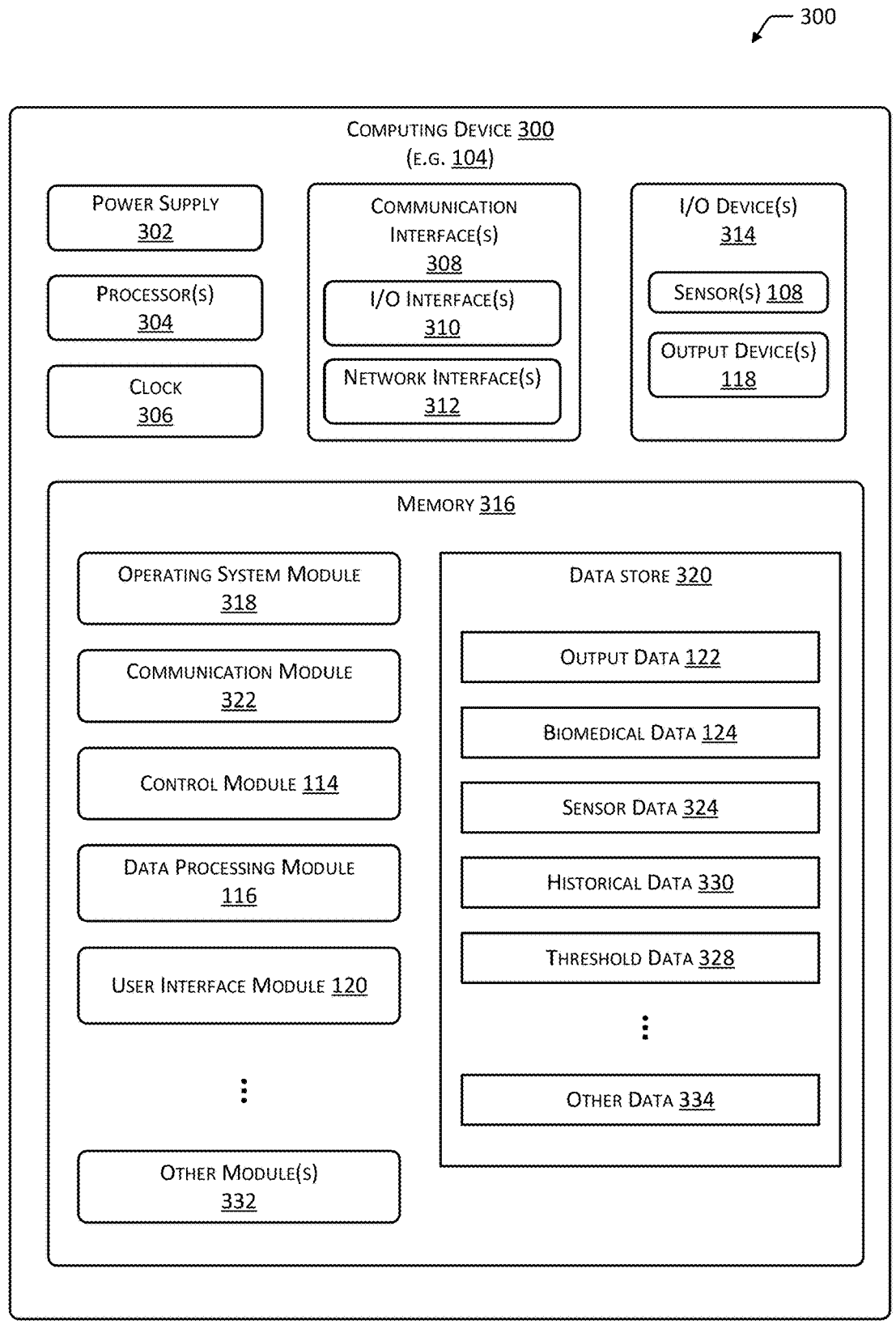
FIG. 3 illustrates a block diagram of a computing device configured to support operation of a wearable device, according to one implementation.

FIG. 3 illustrates a block diagram of a computing device 300 configured to support operation of a wearable device 104. As described above, the computing device 300 may be the wearable device 104.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a camera 108(7), sensors 108, keyboard, mouse, scanner, and so forth. The I/O devices 314 may also include output devices 118 such as one or more of a display device 118(3), printer, audio output device 118(2), and so forth. In some embodiments, the I/O devices 314 may be physically incorporated with the computing device 300 or may be externally placed.

The network interfaces 312 are configured to provide communications between the computing device 300 and other devices, such as the sensors 108, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

The computing device 300 also includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 300, network attached storage devices, and so forth. The data store 320 may store sensor data 324, biomedical data 124, output data 122, or other data 334.

A communication module 322 may be configured to establish communications with one or more of other computing devices 300, the sensors 108, the wearable device 104, or other devices. The communications may be authenticated, encrypted, and so forth. The communication module 322 may also control the communication interfaces 308.

The memory 316 may also store the control module 114. The control module 114 may operate the optical sensor 110 to determine sensor data 324 that is indicative of a cardiac pulse rate, data indicative of oxygen saturation of the user's 102 blood, and so forth. For example, the optical sensor 110 may use an optical emitter such as a light source 132 comprising one or more light emitting diodes (LEDs) and a corresponding optical detector or photodetector 130. The photodetector 130 or a photodiode, may be used by the optical sensor 110 to determine cardiac pulse, determine changes in apparent color of the blood of the user 102 resulting from oxygen binding with hemoglobin in the blood, and so forth.

The memory 316 may store the data processing module 116. The data processing module 116 uses the sensor data 324 as input to generate the biomedical data 124.

Threshold data 328 may be stored in the memory 316. For example, the threshold data 328 may specify threshold values for one or more of: low heart rate, high heart rate, low oxygen saturation, or high oxygen saturation. If the determined heart rate or oxygen saturation of a user exceeds any of the threshold values, then the user interface module 120 may generate an alarm and present that information using the output device 118.

The user interface module 120 provides a user interface using one or more of the I/O devices 314. The user interface module 120 may be used to obtain input from the user 102, present information to the user 102, and so forth. For example, the user interface module 120 may present a graphical user interface on the display device 118(3) and accept user input using the touch sensor 108(4).

The computing device 300 may maintain historical data 330. For example, the historical data 330 may comprise the biomedical data 124, or data from one or more of the sensors 108 obtained at different times. The historical data 330 may be used to provide information about trends or changes over time. For example, the historical data 330 may comprise an indication of average daily heart rate or blood oxygenation levels of the user 102 over a span of several weeks. The user 102 may then use this data to assist in managing a fitness regimen or adjust behaviors toward a healthy lifestyle.

Other modules 332 may also be present in the memory 316, as well as other data 334 in the data store 320.

In different implementations, different computing devices 300 may have different capabilities or capacities. In one implementation, the wearable device 104 may determine the biomedical data 124 and send the biomedical data 124 to other devices. Other combinations of distribution of data processing and functionality may be used in other implementations.

Figure 4:
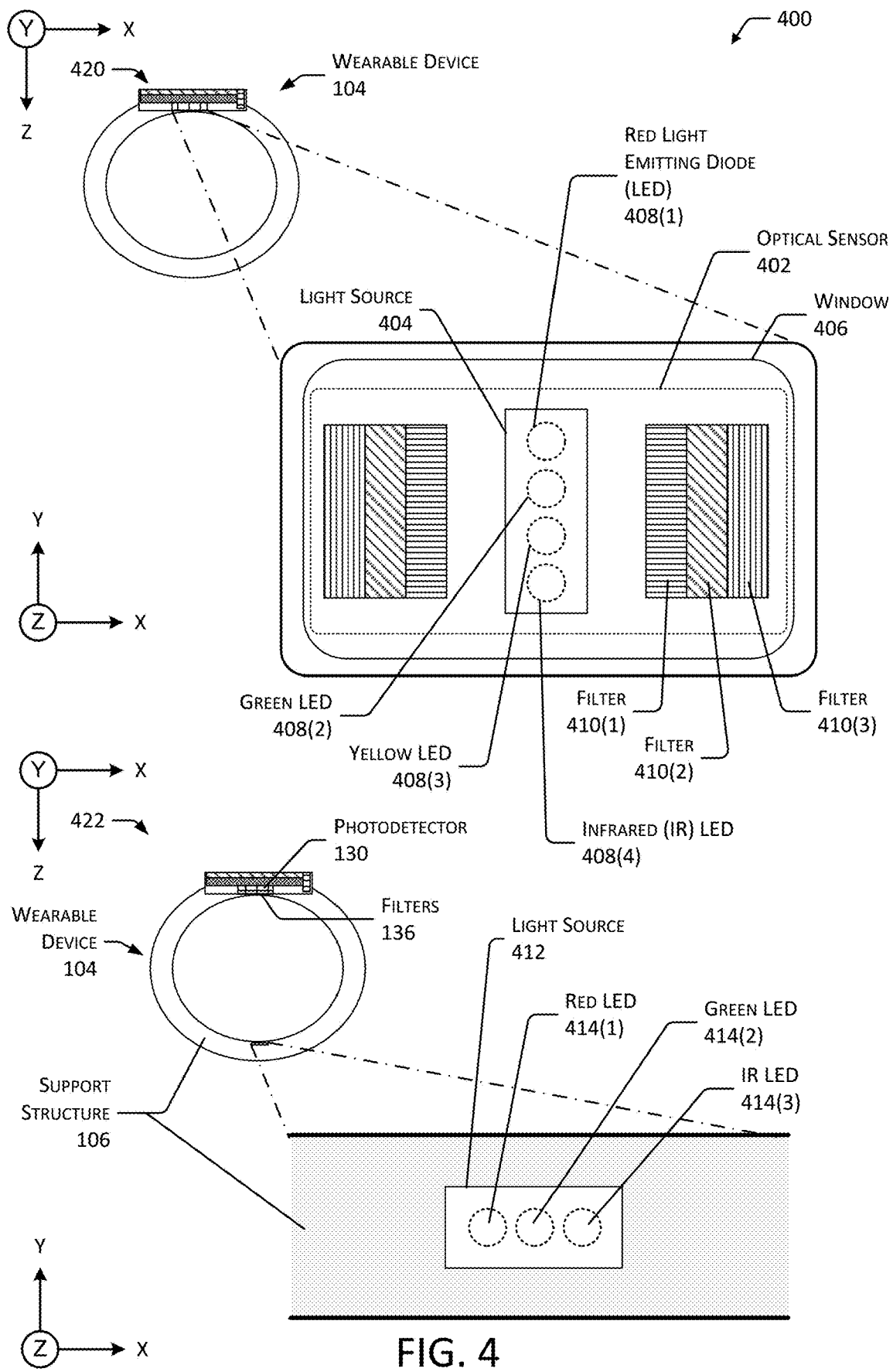
FIG. 4 illustrates two implementations of a wearable device comprising an optical sensor, according to one implementation.

FIG. 4 illustrates, at 400, a first implementation 420 and a second implementation 422 of a wearable device 104 comprising an optical sensor 402.

In the first implementation 420, the wearable device 104 includes an optical sensor 402 and a window 406. The optical sensor 402 may comprise a light source 404 and three filters 410(1-3) applied to a first photodetector, where the light source 404 comprises red, green, yellow, and IR LEDs 408(1-4). In FIG. 4, the first photodetector is not depicted, but is similar to the photodetector 130 in FIG. 1. In this example, the optical sensor 402 comprises additional filters similar to the three filters 410(1-3), and in the interest of clarity, these additional filters are not labeled. Filter 410(1) may be a filter that is transmissive to green wavelengths of light and blocks other wavelengths of light. Filter 410(2) may be a filter that is transmissive to yellow wavelengths of light and blocks other wavelengths of light. Filter 410(3) may be a filter that is transmissive to red or IR wavelengths of light and blocks other wavelengths of light. Different wavelengths of light may reflect within a human body in different ways, where reflected light received at the first photodetector may be used to determine different biomedical data. In other examples, additional filters may be used.

In some implementations, there may be additional filters. For example, a single photodetector may comprise any number of filters, where a limit on the number of filters may be determined by an individual filter area that is transmissive to an individual threshold quantity of diffuse reflectance of a color of light associated with the individual filter. As one example, not depicted, a photodetector may comprise four filters arranged in a 2×2 grid, where each of the four filters is associated with an individual range of light wavelengths. In other examples, there may be other arrangements and configurations of the size and shape of individual filters. In some implementations, a single optical sensor 402 may comprise multiple photodetectors on a same die. For example, for a plurality of filters, the individual filters of the plurality of filters may filter one or more wavelengths of light for one or more photodetectors. An individual filter of the plurality of filters may be transmissive of at least one wavelength of light. In some examples, an individual filter of the plurality of filters may be a notch filter, multimodal notch filter, band-stop filter, or a comb filter.

Similar to the time multiplexing example described above, light received at the first photodetector may be associated with a different color of light depending on a time at which a particular color of light is generated. In this example, at a first time, red light generated by the red LED 408(1) may be received at the first photodetector, where a measured intensity of the received light is associated with a first set of physiological characteristics. At a second time, green light generated by the green LED 408(2) may be received at the first photodetector, where a measured intensity of the received light is associated with a second set of physiological characteristics. At a third time, yellow light generated by the yellow LED 408(3) may be received at the first photodetector, where a measured intensity of the received light is associated with a third set of physiological characteristics. At a fourth time, IR light generated by the IR LED 408(4) may be received at the first photodetector, where a measured intensity of the received light is associated with a fourth set of physiological characteristics.

The second implementation 422 operates in a transmissive mode. Instead of, or in addition to the reflectance of light described above, in some implementations, the wearable device 104 may use transmittance to determine the biomedical data 124. In such an implementation, the light source 132 and the optical sensor 110 may be separated, with a portion of the user 102 arranged in between. For example, the support structure 106 for the wearable device 104 may comprise a light source 412 comprising LEDs 414(1)-(3). The light source 412 within the support structure 106 may emit light that is transmitted through a portion of a user's body and received at the photodetector 130 after passing through the filter(s) 136.

Figure 5:
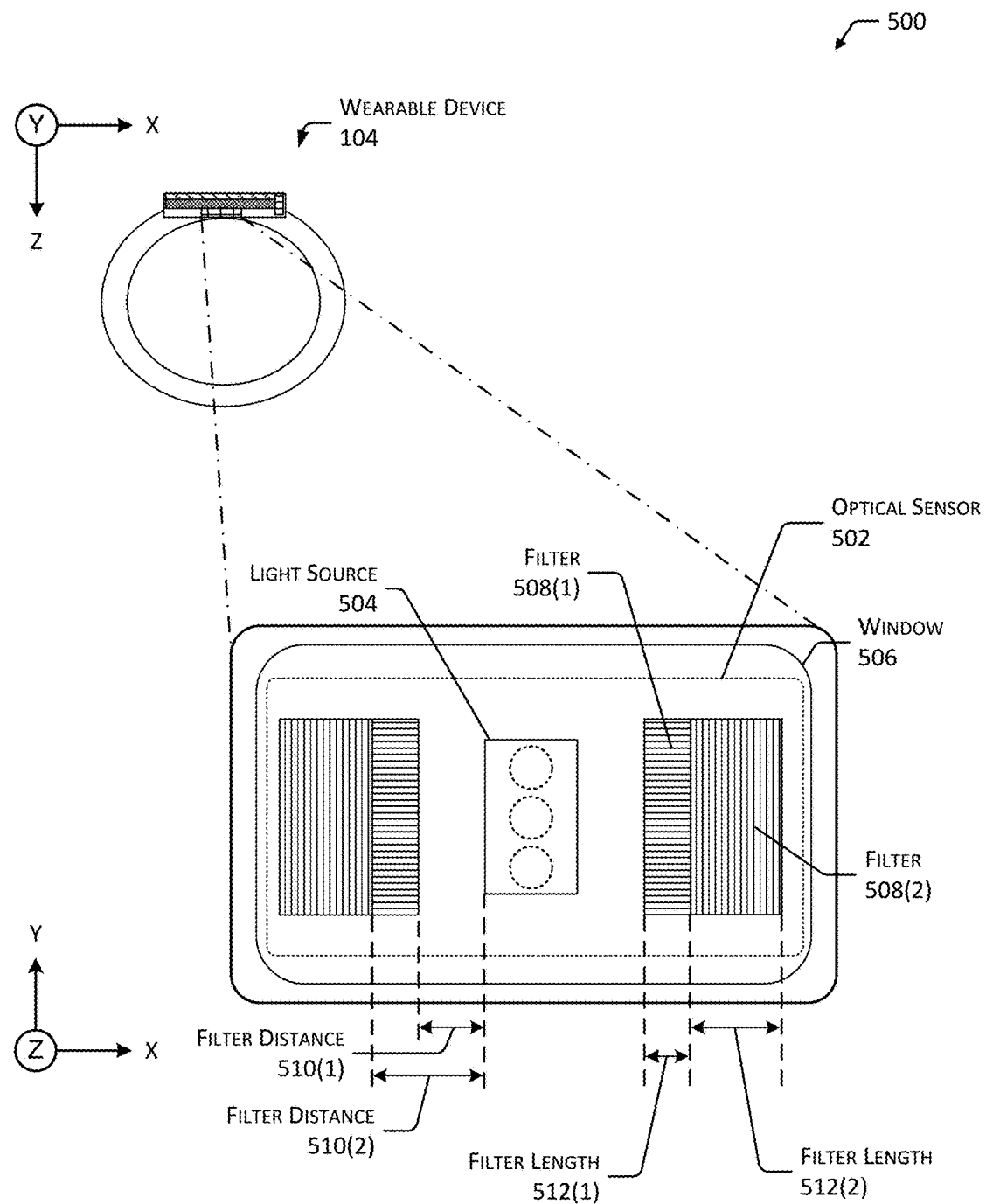
FIG. 5 illustrates a wearable device comprising an optical sensor, according to one implementation.

FIG. 5 illustrates, at 500, one implementation of a wearable device 104 comprising an optical sensor 502.

In this example, the wearable device 104 includes an optical sensor 502 and a window 506. The optical sensor 502 may comprise a light source 504 and two filters 510(1, 2) applied to a first photodetector. In FIG. 5, the first photodetector is not depicted, but is similar to the photodetector 130 in FIG. 1. In this example, the optical sensor 502 comprises additional filters similar to the two filters 508(1, 2), and in the interest of clarity, these additional filters are not labeled. Filter 508(1) may be a filter that is transmissive to green wavelengths of light and blocks other wavelengths of light. Filter 508(2) may be a filter that is transmissive to red or IR wavelengths of light and blocks other wavelengths of light.

The optical sensor 502 in this example comprises two filters 508(1, 2) that cover different portions of a light sensitive area of the first photodetector. The first filter 508(1) is at a first filter distance 510(1) from the light source 504. The second filter 508(2) is at a second filter distance 510(2) from the light source 504. The first filter distance 510(1) is smaller than the second filter distance 510(2) and the first filter 508(1) is closer to the light source than the second filter 508(2).

In this example, a physical area of the first filter 508(1) is smaller than the physical area of the second filter 508(2). The first filter 508(1) has a length along the X-axis of a first filter length 512(1), and the second filter 508(2) has a length along the X-axis of a second filter length 512(2). For example, the first photodetector may have a total light-sensitive area of 3 mm$^2$ (3 millimeters squared). In this example, the first filter 508(1) may comprise ⅓ of the light-sensitive area, and the second filter 508(2) may comprise ⅔ of the light-sensitive area. Other ratios of physical areas of the filters 508(1, 2) may be used.

The size of the physical area of a filter 508(1, 2) may be based on a distance from the light source 504 at which an optical signal for a given wavelength of light satisfies a threshold value of signal quality or signal strength. For example, signal quality for green light is better at a distance from a light source that is closer than signal quality for red light. Based on this, the filter distance 510(1) between the first filter 508(1) and the light source 504 is smaller than the filter distance 510(2) between the second filter 508(2) and the light source 504. In one example, the first filter distance 510(1) may be 3 to 4 mm, and the second filter distance 510(2) may be 6-10 mm.

The size of a filter area may be based on an amount of light signal degradation as a filter is located farther from a light source. For example, based on the first filter length 512(1), the first filter 508(1) may be transmissive of X % of green light emitted by the light source 504, where X surpasses a threshold value. To increase or decrease X to reach the threshold value, the first filter length 512(1) may be respectively increased or decreased.

Figure 6:
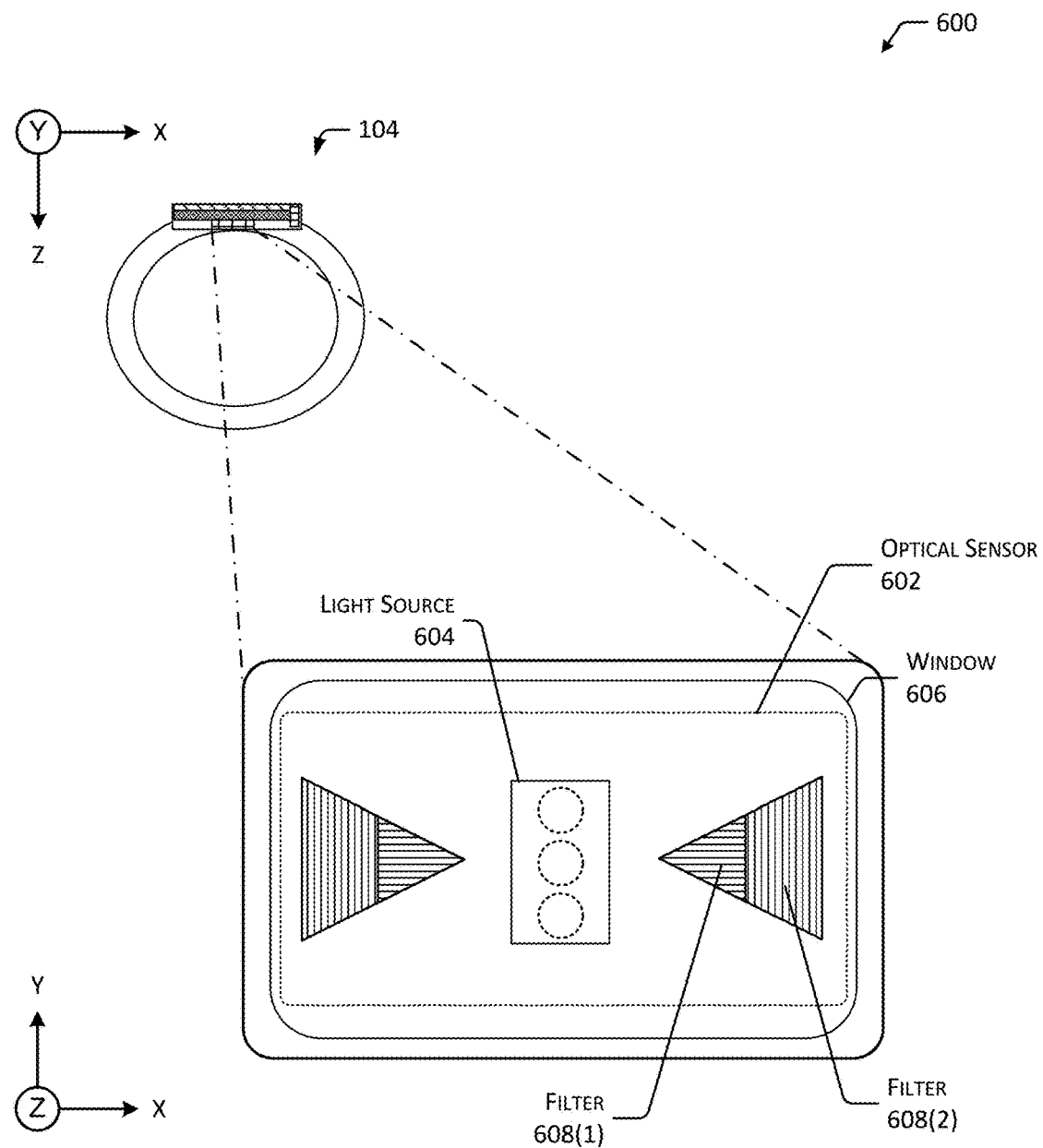
FIG. 6 illustrates a wearable device comprising an optical sensor, according to one implementation.

FIG. 6 illustrates, at 600, one implementation of a wearable device 104 comprising an optical sensor 602.

In this example, the wearable device 104 includes an optical sensor 602 and a window 606. The optical sensor 602 may comprise a light source 604 and two filters 608(1, 2) applied to a first photodetector. In FIG. 6, the first photodetector is not depicted, but is similar to the photodetector 130 in FIG. 1. In this example, the optical sensor 602 comprises additional filters similar to the two filters 608(1, 2), and in the interest of clarity, these additional filters are not labeled. Filter 608(1) may be a filter that is transmissive to green wavelengths of light and blocks other wavelengths of light. Filter 608(2) may be a filter that is transmissive to red or IR wavelengths of light and blocks other wavelengths of light.

Generally, the first photodetector may be fabricated to be different shapes, such as a wedge, a triangle, a rectangle, a circle, or an oval. In this example, the shape of the first photodetector is triangular. In other examples, the shape of the first photodetector may be rectangular, such as the photodetector 130 depicted in FIG. 1. The shape of the first photodetector may also be circular. For example, a shape of a photodetector may be based on how light intended to be received by an individual filter is reflected and scatters after penetrating a user's skin.

Figure 7:
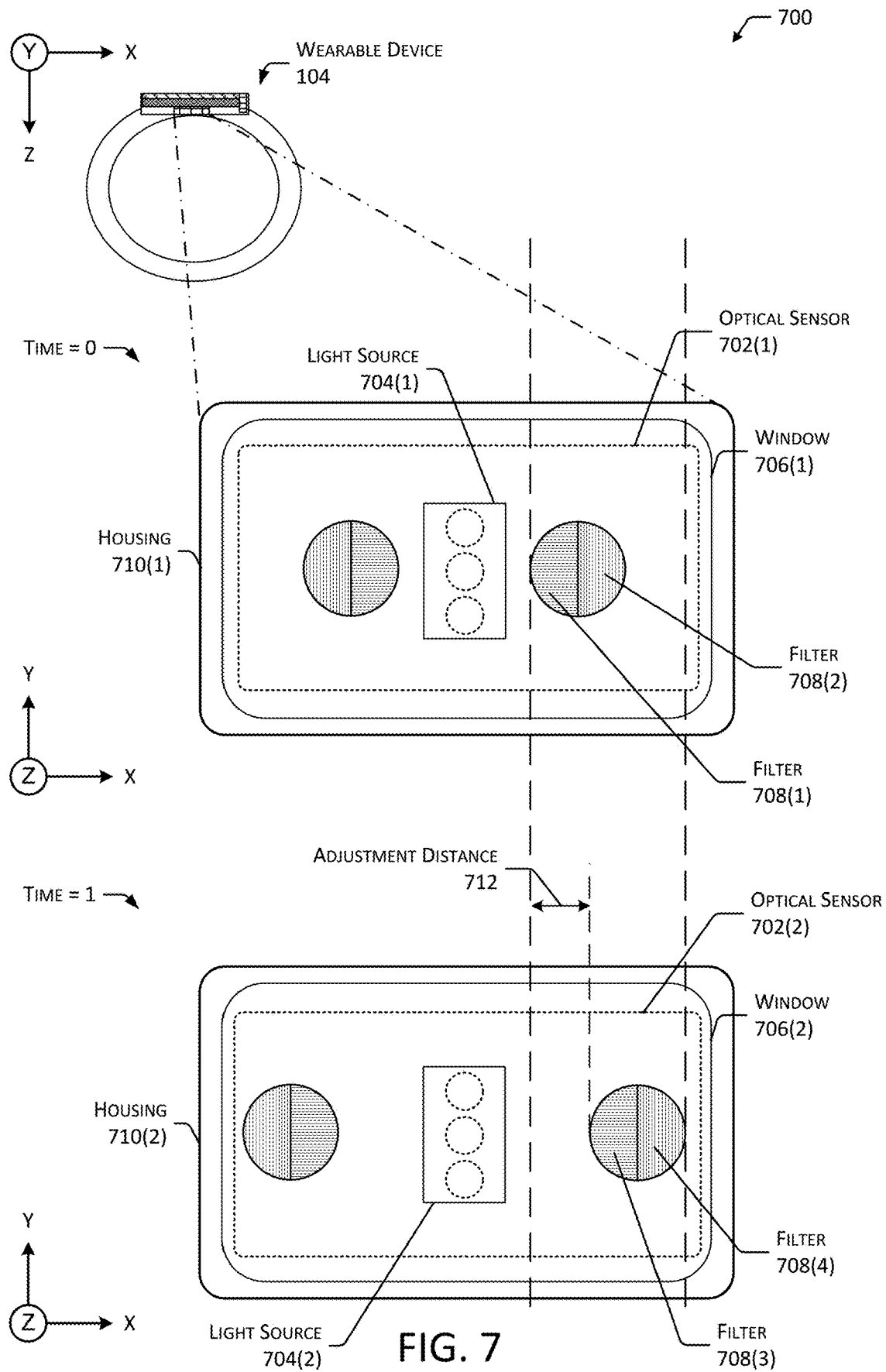
FIG. 7 illustrates a wearable device comprising an optical sensor, according to one implementation.

FIG. 7 illustrates, at 700, one implementation of a wearable device 104 comprising an optical sensor 702.

In this example, a first assembly may comprise a first housing 710(1) that comprises a first optical sensor 702(1) and a window 706(1). The first optical sensor 702(1) comprises a first light source 704(1) and two filters 708(1, 2) applied to a first photodetector. In FIG. 7, the first photodetector is not depicted, but is similar to the photodetector 130 in FIG. 1. In this example, the optical sensor 702(1) comprises additional filters similar to the two filters 708(1, 2), and in the interest of clarity, these additional filters are not labeled. The first assembly may be a field-replaceable unit.

The second assembly may comprise a second housing 710(2) that comprises a second optical sensor 702(2) and a window 706(2). The second optical sensor 702(2) comprises a second light source 704(2) and two filters 708(3, 4) applied to a second photodetector. The second assembly may also be a field-replaceable unit.

Different users may have different physiological characteristics that affect how light travels through a body and how light is absorbed and reflected. In some examples, quality of an optical signal received from emitting green light is better for a particular user 102 at a first distance than at a second distance. Similarly, for an optical signal received from emitting red or IR light, the quality of an optical signal received may be better, depending on a user's particular physiology, at a first distance than at a second distance. In such a case, the wearable device 104 may determine more accurate biomedical data for the user 102 if the relative locations of the light source 704 and a photodetector comprising filters 708(1, 2) is adjusted by an adjustment distance 712. The adjustment distance 712 may be a difference between the first distance and the second distance.

In this example, at a first time, time=0, the wearable device 104 includes optical sensor 702(1) and a window 706(1). The optical sensor 702(1) comprises a light source 704(1) and filters including filters 708(1, 2). Filter 708(1) may be a filter that is transmissive to green wavelengths of light and blocks other wavelengths of light. Filter 708(2) may be a filter that is transmissive to red or IR wavelengths of light and blocks other wavelengths of light.

The first housing 710(1) may be a default housing. The first housing 710(1) may be attached or removed from a body of the wearable device 104 using different mechanical mechanisms. For example, the first housing 710(1) may attach or be removed using screws or may attach or be removed using some other type of fastener. In this example, a difference between the first housing 710(1) and the second housing 710(2) may be a change in distance between a first difference and a second difference. The first difference may be the distance between the light source 704(1) and the first photodetector comprising filters 708(1, 2), and the second difference may be the distance between the light source 704(2) and the second photodetector comprising filters 708(3, 4). The change in distance may be represented by the adjustment distance 712.

Continuing with this example, at the second time, time=1, the first assembly comprising the first housing 710(1) has been replaced by the second assembly comprising the second housing 710(2). The first assembly may be replaced as a field replaceable unit by a service technician, such as a service technician available at a retail outlet that services the wearable device 104. Based on the positioning of the filters in the second housing 710(2) resulting in improved quality of optical signals used by the optical sensor 702(2), the user 102 may be provided with more accurate determination of biomedical data.

At the second time, the wearable device 104 includes the optical sensor 702(2) and a window 706(2). The optical sensor 702(2) comprises a light source 704(2) and filters including filters 708(3, 4). Filter 708(3) may be a filter that is transmissive to green wavelengths of light and blocks other wavelengths of light. Filter 708(4) may be a filter that is transmissive to red or IR wavelengths of light and blocks other wavelengths of light.

At the second time, in other implementations, the wearable device 104 may maintain a same optical sensor 702 and mechanically adjust a physical location of the photodetector relative to the light source 704(1). In this example, the photodetector is not replaced by a different photodetector to achieve a different distance configuration between the light source 704(1) and an associated photodetector. For example, a technician may remove the window 706(1) from the housing 710(1) to access a mechanism affixing the photodetector. For example, the photodetector may be affixed to the housing 710(1) using one or more screws, where a technician may affix the photodetector in one or more locations within the housing 710(1). In this example, the housing 710(1) comprises a plurality of locations that position the photodetector at a plurality of distances relative to the light source 704(1).

Figure 8:
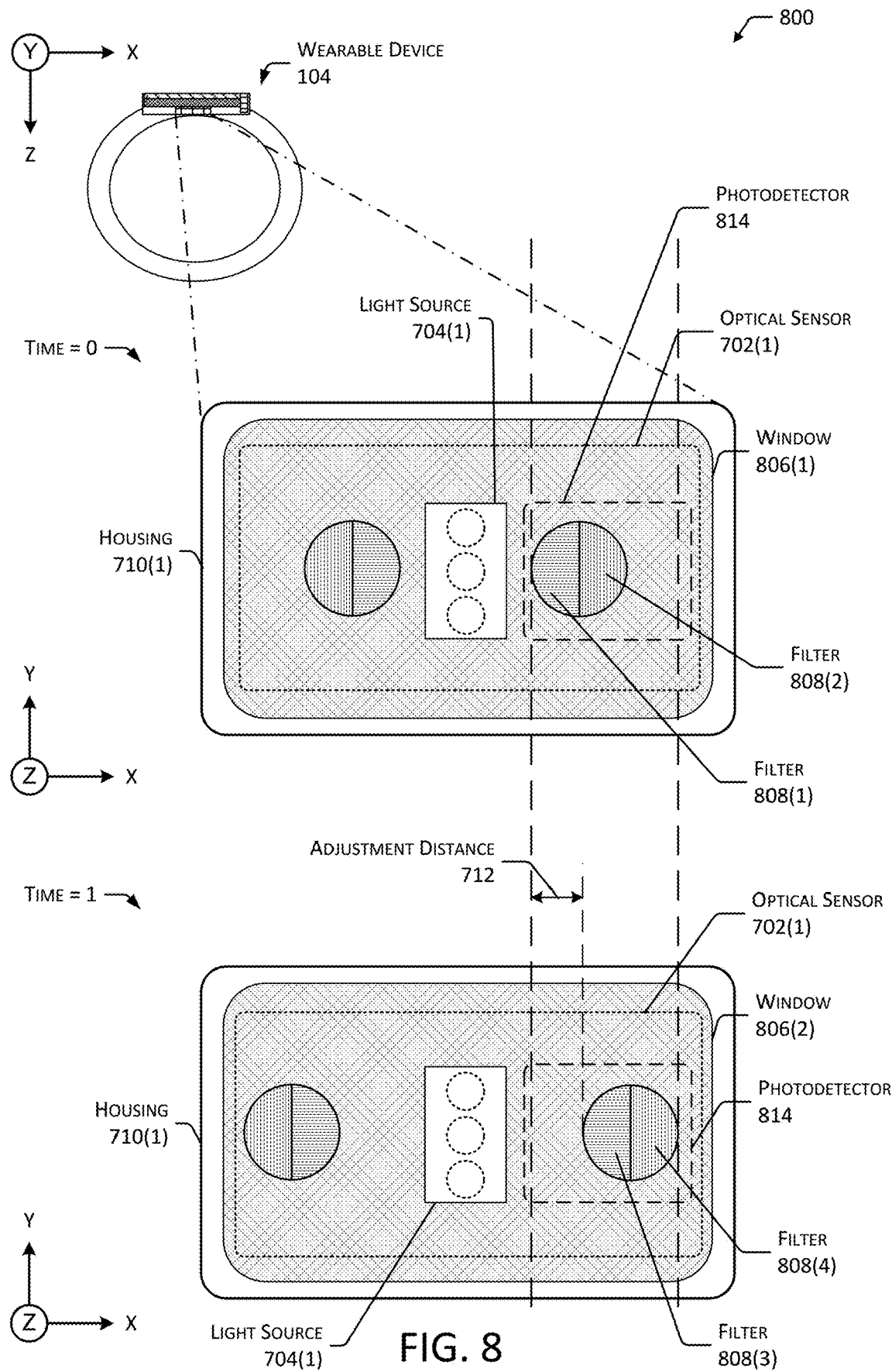
FIG. 8 illustrates a wearable device comprising an optical sensor, according to one implementation.

FIG. 8 illustrates, at 800, one implementation of a wearable device 104 comprising an optical sensor 702.

In this example, at a first time=0, a first housing 710(1) comprises a first optical sensor 702(1) and a first window 806(1). The first optical sensor 702(1) comprises a first light source 704(1) and a photodetector 814. The first window 806(1) comprises multiple areas with filters, including filters 808(1, 2). The first window 806(1) may be a field-replaceable unit.

At a second time=1, the first housing 710(1) comprises the first optical sensor 702(1) and a second window 806(2) that has replaced the first window 806(1).

Different users may have different physiological characteristics that affect how light travels through a body and how light is absorbed, reflected, or scattered. In some examples, quality of an optical signal received from emitting green light is better for a particular user at a first distance than a second distance. Similarly, for an optical signal received from emitting red or IR light, the quality of an optical signal received may depend on a user's physiology. For example, the quality of an optical signal resulting from receiving red or IR light may be improved if a filter is at a third distance from a light source than at a fourth distance from the light source. In such a case, the wearable device 104 may determine more accurate biomedical data for the user 102 if the relative locations of the light source 704 and a light measurement is adjusted by an adjustment distance 712. The adjustment distance 712 may be a difference between the first distance and the second distance.

In some implementations, a distance between a light source 704(1) and one or more filters 808(1, 2) may be adjusted by the adjustment distance 712 by replacing a window 806(1) of the housing 710(1). The window 806(1) may be coated with multiple filters 808(1, 2) instead of the light-sensitive area of a photodetector 814 being coated with one or more filters. For example, an outward facing or inward facing surface of the window 806(1) may be coated with a filter that blocks all light except for a first area for the light source 704(1) and one or more areas that are coated with different one or more filters.

In this example, the first area for the window 806(1) may have no filters and be sized and positioned to correspond to a position, size, and dimension of the light source 704(1). The one or more areas coated with the different one or more filters may be positioned and shaped over one or more photodetectors, such as photodetector 814. For example, two filters 808(1, 2) may be located on the first window 806(1) as depicted in FIG. 8. Filter 808(1) may be in a first location and area on the first window 806(1) and may be transmissive to a first color light and allow the first color of light to pass through to the photodetector 814. Filter 808(2) may be in a second location and area on the first window 806(1) and may be transmissive to a second color of light and allow the second color of light to pass through to the photodetector 814. In this example, the first window 806(1) may be a field-replaceable unit and may be replaced with a customized window that has filters in a different location with respect to the light source 704(1), where the filters in the customized window may be of a different size, shape, or transmissive to one or more colors.

In this example, at a first time, time=0, the wearable device 104 includes an optical sensor 702(1) and a first window 806(1) comprising filters 808(1, 2). Filter 808(1) may be a filter that is transmissive to green wavelengths of light and blocks other wavelengths of light. Filter 808(2) may be a filter that is transmissive to red or IR wavelengths of light and blocks other wavelengths of light.

The first window 806(1) may be a default window. The first window 806(1) may be attached or removed from a body of the wearable device 104 using different mechanical mechanisms. For example, the first window 806(1) may attach or be removed using screws or may attach or be removed using some other type of fastener. In this example, a difference between the first window 806(1) and the second window 806(2) may be a change in distance of filter locations between a first difference and a second difference. The first difference may be the distance between the light source 704(1) and the filters 808(1, 2), and the second difference may be the distance between the light source 704(2) and the filter 808(3, 4). The change in distance may be represented by the adjustment distance 712.

Continuing with this example, at the second time, the first window 806(1) has been replaced by the second window 806(2). The first window may be replaced as a field replaceable unit by a service technician, such as a service technician available at a retail outlet that services the wearable device 104. Based on the positioning of the filters in the second window 806(2) resulting in improved quality of optical signals used by the optical sensor 702(1), the user 102 may be provided with more accurate determination of biomedical data.

At the second time, time=1, the wearable device 104 includes optical sensors 702(1) and the window 806(2).

Figure 9:
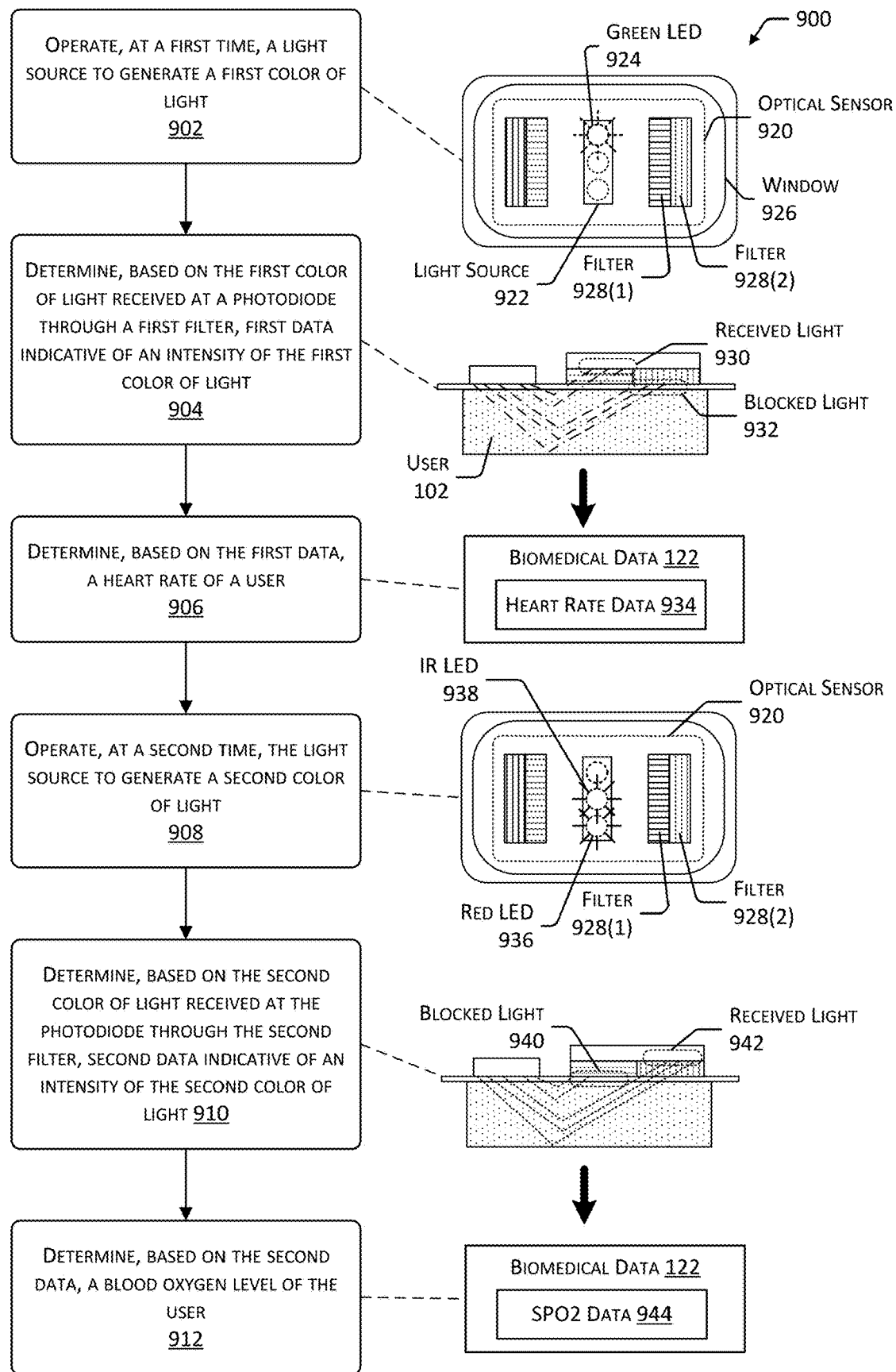
FIG. 9 illustrates a flow diagram of a process of using a single optical sensor comprising multiple filters, according to one implementation.

FIG. 9 illustrates a flow diagram 900 of a process of using a single optical sensor comprising multiple filters, according to one implementation. The process may be implemented by the wearable device 104.

In this example, the wearable device 104 comprises: a support structure that retains the wearable device 104 proximate to a user 102; an optical sensor 920 comprising a light source 922; a window 926; and a first photodetector comprising a light-sensitive area, a first filter 928(1), and a second filter 928(2). The first photodetector may be a photodiode or some other form of photodetector. The light source 922 comprises a green LED 924, a red LED 936, and an IR LED 938. In some examples, the optical sensor 920, the control module 114, or both may be implemented by electronic circuitry.

The first filter 928(1) may be at a first distance from the light source 922. The first filter 928(1) may allow a first color of light to be received at a first portion of the light-sensitive area. The first filter 928(1) may block a second color of light from being received at the first portion of the light-sensitive area. The first color of light may be green. The second color of light may be red.

The second filter 928(2) may be at a second distance from the light source 922. The second filter 928(2) may allow a second color of light to be received at a second portion of the light-sensitive area. The second filter 928(2) may block a first color of light from being received at the first portion of the light-sensitive area. The second distance may be larger than the first distance.

At 902, the control module 114 may operate, at a first time, the light source 922 to generate a first color of light. For example, at the first time, the control module 114 may execute computer instructions that provide electrical power to the green LED 924 for a first period of time, where the power to the green LED 924 generates the first color of light. The first color of light may be a green wavelength of light. During the first period of time while the green LED 924 is emitting green color light, the second filter 928(2) is blocking the green color light, depicted as blocked light 932.

At 904, the control module 114 may determine, based on the first color of light received at the photodiode through the first filter 928(1), first data indicative of an intensity of the first color of light. For example, the optical sensor 920 may produce analog output used to determine a value indicative of the intensity of the first color of light. The first color of light may be generated for the first period of time that allows for changes in blood volume of one or more arteries of the user 102. The changes in blood volume correspond to a heartbeat, or heart rate, of the user 102. The first color of light may be emitted from the green LED 924 and penetrate the skin of the user 102. A portion of the emitted light may be absorbed, a portion may be scattered, and a portion may be reflected into the first filter 928(1). As the volume of blood in arteries of the user 102 changes, the portion of the light reflected into the first filter 928(1) may change. The changes in the portion of light reflected into the first filter 928(1) result in changes in electrical current produced by the first photodetector. The first data may be indicative of the changes in electrical current from the first photodetector based on the received light 930.

At 906, the control module 114 may determine, based on the first data, a heart rate of the user 102. The changes in detected light received at the first filter 928(1), as indicated by the first data, are associated with changes in electrical current used to determine heart rate data 934 for the user 102. For example, different rates of change in electrical current may be associated with individual heart rates.

At 908, the control module 114 may operate, at a second time, the light source 922 to generate a second color of light. For example, at the second time, the control module 114 may execute computer instructions that provide electrical power to the red LED 936 for a second period of time, where the power to the red LED 936 generates the second color of light. The second color of light may be a red wavelength of light. During the second period of time while the red LED 936 is emitting red color light, the first filter 928(1) is blocking the red color light and the IR light, as depicted as blocked light 940. In some examples, at the second time, the control module 114 may also operate the light source 922 to generate an IR wavelength of light. For example, at the second time, the control module 114 may generate IR light by powering the IR LED 938. Using both red light and IR light is used to generate data indicating distinctive absorption properties of oxygenated and deoxygenated hemoglobin used to determine oxygen saturation or a blood oxygen level.

At 910, the control module 114 may, based on the second color of light received at the photodiode through the second filter 928(2), second data indicative of an intensity of the second color of light. The second data may be indicative of an amount electrical current from the first photodetector based on the received light 942.

At 912, the control module 114 may determine, based on the second data, a blood oxygen level of the user 102. For example, hemoglobin is an oxygen-transport protein in red blood cells, and two forms of hemoglobin are oxygenated hemoglobin and deoxygenated hemoglobin. Oxygen saturation (SPO2) may be a measure of the amount of oxygen in capillary blood reachable by the emitted light from the light source 922. Oxygen saturation may be determined as a percentage of the amount of oxygenated hemoglobin to total hemoglobin. Oxygen saturation may be determined based on modulation of transmitted light by absorption of pulsatile arterial blood and different absorption characteristics of oxygenated hemoglobin and deoxygenated hemoglobin for different wavelengths of light. Pulsatile arterial blood absorbs and modulates the light passing through skin and other tissue of the user 102 and forms a first signal generated by the first photodetector. A second signal generated by the first photodetector is based on effects of light absorbed by other blood and tissue components of the user 102, such as venous and capillary blood, bone, and water. The first signal and the second signal may be used to determine light absorption data to determine blood oxygen levels or oxygen saturation, depicted as SPO2 data 944.

In this example, the level of oxygen in a user's blood has an effect on how much of the first color light emitted from the red LED 936, is reflected into the second filter 928(2). The second color of light may be emitted from the red LED 936 and penetrate the skin of the user 102, where IR light emitted from the IR LED 938 is also reflected into the second filter 928(2). A portion of the emitted light may be absorbed, a portion may be scattered, and a portion may be reflected into the second filter 928(2). The received light at the second filter 908(2) is depicted as received light 942. For different oxygen levels in the blood of the user 102, different portions of the light reflected into the second filter 928(2) may be detected by the first photodetector.

In this example, output indicative of the heart rate data 934 or the blood oxygen level, SPO2 data 944, may be presented. In one implementation, the user interface module 120 may generate output data 122 that is used by the one or more output devices 118 to present output to the user 102. For example, a graphical indication may be provided using a display device 118(3).

While the system and techniques described herein are used with respect to measure humans, it is understood that these techniques may be used to monitor other types of animals. In some implementations, the systems and techniques may be used to characterize biological data or physiological data of other objects or users, such as plants or animals.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
   a support structure that retains the wearable device proximate to a user;
   a light source;
   a photodiode comprising a light-sensitive area;
   a first filter that is at a first distance from the light source, wherein the first filter:
   allows a first color of light to be received at a first portion of the light-sensitive area, and
   blocks a second color of light from being received at the first portion of the light-sensitive area;
   a second filter that is at a second distance from the light source, wherein the second filter:
   allows the second color of light to be received at a second portion of the light-sensitive area, and
   blocks the first color of light from being received at the second portion of the light-sensitive area;
   one or more memories storing computer-executable instructions; and
   one or more processors, wherein the one or more processors execute the computer-executable instructions to:
   operate, at a first time, the light source to generate the first color of light;
   determine, based on the first color of light received at the photodiode through the first filter, first data indicative of an intensity of the first color of light at the first time;
   operate, at a second time, the light source to generate the second color of light;
   determine, based on the second color of light received at the photodiode through the second filter, second data indicative of an intensity of the second color of light at the second time;
   determine, based on the first data, a heart rate of the user; and
   determine, based on the second data, a blood oxygen level of the user.

2. The wearable device of claim 1, wherein, based on the first color of light being associated with a shorter wavelength than the second color of light, the first distance is less than the second distance, wherein the first color of light is green, and wherein the second color of light is red.

3. The wearable device of claim 1, further comprising:
   a housing comprising a plurality of locations that position the photodiode relative to the light source, wherein individual locations of the plurality of locations are associated with different physiological characteristics that affect penetration of different wavelengths of light into skin.

4. A wearable device comprising:
   a light source;
   a first detector comprising:
   a light-sensitive area;
   a first filter at a first location with respect to the light-sensitive area, wherein:
   the first filter is transmissive to a first wavelength, and
   the first location is at a first distance from the light source; and
   a second filter at a second location with respect to the light-sensitive area, wherein:
   the second filter is transmissive to a second wavelength, and
   the second location is at a second distance from the light source,
   further wherein the second distance is greater than the first distance; and
   electronic circuitry to operate the light source and the first detector to:
   operate the light source at a first time to generate first light at the first wavelength;
   determine, based on at least a portion of the first light being received through the first filter, first output from the first detector at the first time;
   operate the light source at a second time to generate second light at the second wavelength; and
   determine, based on at least a portion of the second light being received through the second filter, second output from the first detector at the second time.

5. The wearable device of claim 4, wherein a first portion of the light-sensitive area is indicative of a size of the first filter, wherein a second portion of the light-sensitive area is indicative of a size of the second filter, wherein the first portion is smaller than the second portion, and wherein the first portion and the first distance are based on diffuse reflection properties of the first wavelength with respect to user physiology.

6. The wearable device of claim 4, wherein the first filter comprises a short-pass dielectric coating over the light-sensitive area of the first detector, and wherein the second filter comprises a long-pass dielectric coating over the light-sensitive area of the first detector.

7. The wearable device of claim 4, wherein the first detector further comprises:
   a third filter at a third location with respect to the light-sensitive area, wherein:
   the third filter is transmissive to a third wavelength, and
   the third location is at a third distance from the light source; and
   wherein the third location is between the first location and the second location.

8. The wearable device of claim 4, wherein the electronic circuitry further operates the light source and the first detector to:
   at a third time while the light source is inactive, determine third output from the first detector;
   determine first data based on the first output and the third output;
   determine second data based on the second output and the third output; and
   determine biomedical data based on the first data and the second data.

9. The wearable device of claim 4, further comprising:
   a second detector;
   wherein the electronic circuitry operates the second detector to:
   at the first time, determine third output from the second detector;
   determine first biomedical data based on the first output and the third output;
   at the second time, determine fourth output from the second detector; and
   determine second biomedical data based on the second output and the fourth output.

10. The wearable device of claim 4, further comprising:
    a housing comprising the light source and the first detector,
    wherein the housing comprises a plurality of locations that position the first detector relative to the light source, wherein a third location of the plurality of locations is associated with the first distance and the second distance, wherein the third location is associated with a first set of physiological characteristics of a first user, and wherein a fourth location of the plurality of locations is associated with a second set of physiological characteristics of a second user.

11. The wearable device of claim 4, further comprising:
a field-replaceable housing comprising the light source and the first detector.

12. The wearable device of claim 4, wherein a shape of the light-sensitive area is one of: a rectangle, a wedge, or a circle.

13. A device comprising:
a light source;
a first detector comprising:
  a light-sensitive area;
  a plurality of filters, wherein
    individual filters of the plurality of filters are transmissive to at least one wavelength of light, and
    individual filters of the plurality of filters are located at individual distances from the light source; and
electronic circuitry to:
  operate the light source at a first time to generate first light at a first wavelength;
  determine first output from the first detector at the first time;
  operate the light source at a second time to generate second light at a second wavelength; and
  determine second output from the first detector at the second time.

14. The device of claim 13, wherein a first portion of the light-sensitive area is indicative of a size of a first filter of the plurality of filters, wherein the first filter is at a first distance from the light source, wherein a second portion of the light-sensitive area is indicative of a size of a second filter of the plurality of filters, wherein the second filter is at a second distance from the light source, wherein the first portion is smaller than the second portion, and wherein the first portion and the first distance are based on reflective properties of the first wavelength with respect to user physiology.

15. The device of claim 13, wherein a first filter of the plurality of filters comprises a short-pass dielectric coating over the light-sensitive area of the first detector, and wherein a second filter of the plurality of filters comprises a long-pass dielectric coating over the light-sensitive area of the first detector.

16. The device of claim 13, wherein the plurality of filters comprises:
a first filter at a first location with respect to the light-sensitive area, wherein:
  the first filter is transmissive to the first wavelength, and
  the first location is at a first distance from the light source;
a second filter at a second location with respect to the light-sensitive area, wherein:
  the second filter is transmissive to the second wavelength, and
  the second location is at a second distance from the light source, further wherein the second distance is greater than the first distance; and
a third filter at a third location with respect to the light-sensitive area, wherein:
  the third filter is transmissive to a third wavelength, and
  the third location is at a third distance from the light source;
wherein the third location is between the first location and the second location; and
wherein the third wavelength is associated with a yellow color.

17. The device of claim 13, wherein the electronic circuitry further operates the light source and the first detector to:
at a third time while the light source is inactive, determine third output from the first detector;
determine first data based on the first output and the third output;
determine second data based on the second output and the third output; and
determine biomedical data based on the first data and the second data.

18. The device of claim 13, further comprising:
a second detector;
wherein the electronic circuitry operates the second detector to:
  at the first time, determine third output from the second detector;
  determine first biomedical data based on the first output and the third output;
  at the second time, determine fourth output from the second detector; and
  determine second biomedical data based on the second output and the fourth output.

19. The device of claim 13, further comprising:
a housing comprising the light source and the first detector,
  wherein the housing comprises a plurality of locations that position the first detector relative to the light source;
wherein the plurality of filters comprises:
  a first filter at a first location with respect to the light-sensitive area, wherein:
    the first filter is transmissive to the first wavelength, and
    the first location is at a first distance from the light source; and
  a second filter at a second location with respect to the light-sensitive area, wherein:
    the second filter is transmissive to the second wavelength, and
    the second location is at a second distance from the light source,
    further wherein the second distance is greater than the first distance; and
wherein a third location of the plurality of locations is associated with the first distance and the second distance.

20. The device of claim 13, further comprising:
a replaceable housing comprising the light source and the first detector.

* * * * *